United States Patent [19]

Kopito

[11] 4,300,555
[45] Nov. 17, 1981

[54] PRODUCT, COMPOSITION, AND PROCESS FOR ANORECTAL PROPHYLACTIC AND/OR THERAPEUTIC CARE

[76] Inventor: Louis Kopito, 204 Clinton Rd., Brookline, Mass. 02146

[21] Appl. No.: 104,131

[22] Filed: Dec. 17, 1979

[51] Int. Cl.³ ............................................. A61M 7/00
[52] U.S. Cl. .................................................. 128/248
[58] Field of Search .............. 128/248, 239, 232, 260, 128/66; 222/215; 239/327, 590.3

[56] References Cited

U.S. PATENT DOCUMENTS 2,784,882  3/1957  Du Bois ........................... 222/215

*Primary Examiner*—John D. Yasko
*Attorney, Agent, or Firm*—Morse, Altman, Oates & Dacey

[57] ABSTRACT

An aqueous formulation for topical care of the anorectal region comprises a specified low concentration of ionic zinc, a surfactant, and other agents. Preferably, the formulation is applied as a jet through a nozzle and from a container of specific design. Pharmaceutical and mechanical details and interactions are described.

13 Claims, 3 Drawing Figures

PRODUCT, COMPOSITION, AND PROCESS FOR ANORECTAL PROPHYLACTIC AND/OR THERAPEUTIC CARE

REFERENCE TO DISCLOSURE DOCUMENT

The present invention is disclosed in part in Disclosure Document No. 079,020, filed Mar. 19, 1979.

BACKGROUND OF THE INVENTION

Field of the Invention

The present invention relates to pharmaceutical formulations, mechanical structures and their combination for routine anal hygiene and/or ambulatory medical care. The present invention more particularly relates to the clinical and/or post-operative care of hemorrhoidal tissue.

Background of the Invention

The formation of internal and external hemorrhoids is a lifelong process affecting a large proportion (some estimates indicate over 70%) of American adults over the age of 50. Many believe that the primary cause of external hemorrhoids is the abrading action of toilet tissue and the presence of residual fecal matter after wiping with toilet tissue. Several studies have indicated that diet, heredity, and various extraneous factors have played a lesser role in the initiation of fissures in and other traumas to the skin, by which external hemorrhoids are generated and aggravated. It has been demonstrated that the use of a sitz bath immediately after defecation is capable of the temporary arrest of hemorrhoidal proliferation. In a substantial number of patients, this treatment also resulted in reversal of the pathological process and in the gradual shrinking of affected tissue. However, the use of a sitz bath is not feasible other than in a hospital or restricted home setting. Furthermore, the relief provided by such sitz bath use generally has been temporary, lasting for at most several hours. The foregoing problems stem from the particular nature of the anorectal region.

The anorectal region is characterized by a high concentration apocrine sweat glands. These relatively large sweat glands respond to emotional as well as temperature stimuli. Unlike the eccrine sweat glands, which produce a clear, low viscosity fluid, the apocrine sweat they produce is a viscous, milky fluid that hinders the healing of open skin fissures. With the initiation of a break in the skin surface, the maintenance of personal hygiene becomes more difficult and painful. The process of hemorrhoid formation often accelerates despite the application of currently available protective creams and ointments because the initially beneficial action of these compositions is interrupted immediately after defecation. Often, the condition becomes irreversible, in which case surgical removal of the active, bleeding hemorrhoidal tissue is essential in order to prevent more serious consequences. While the surgical procedure is relatively safe and painless, the recovery period generally, and the first defecations during the recovery period tend to be extremely painful and require utmost hygienic care to prevent infection. In summary, there has been no simple method for the anal care of an ambulatory patient who has undergone a hemorrhoidectomy. Consequently, such a patient has been immobilized at home or hospital for longer periods than are indicated medically.

BRIEF SUMMARY OF THE INVENTION

The primary object of the present invention is to provide a topical formulation and a mechanical dispenser which aid in such processes as: ambulatory, post-hemorrhoidectomy care; prophylactic routine maintenance of anorectal hygiene; alleviation and possible reversal of hemorrhoidal formations; temporary relief of pruritus ani (rectal itch); and removal and neutralization of apocrine sweat following prolonged sitting or vigorous exercise. The topical formulation contains, in an aqueous vehicle a low concentration, i.e. less than ten percent by total weight, of active agents including a healing accelerator, a surfactant, a film former, a lubricant, and a disinfectant, the nature and function of which leave a thin residual film after being applied. The mechanical dispenser is provided with a reversely bent nozzle that is directed toward the anorectal area when the dispenser is inverted and held manually, the nozzle being designed to eject a jet of maximal velocity and minimal flow rate to remove and neutralize feces, sweat, and soap residues having a basic pH.

Other objects of the present invention will in part be obvious and will in part appear hereinafter.

The invention accordingly comprises the compositions, products, and processes, together with their components, parts, steps, and interrelationships, which are exemplified in the present disclosure, the scope of which will be indicated in the appended claims.

BRIEF DESCRIPTION OF THE DRAWINGS

For a fuller understanding of the nature and objects of the present invention, reference is made to the following detailed description which is to be taken in conjunction with the annexed drawings, wherein.

DETAILED DESCRIPTION OF THE PREFERRED EMBODIMENT

Figures 1, 2, 3:
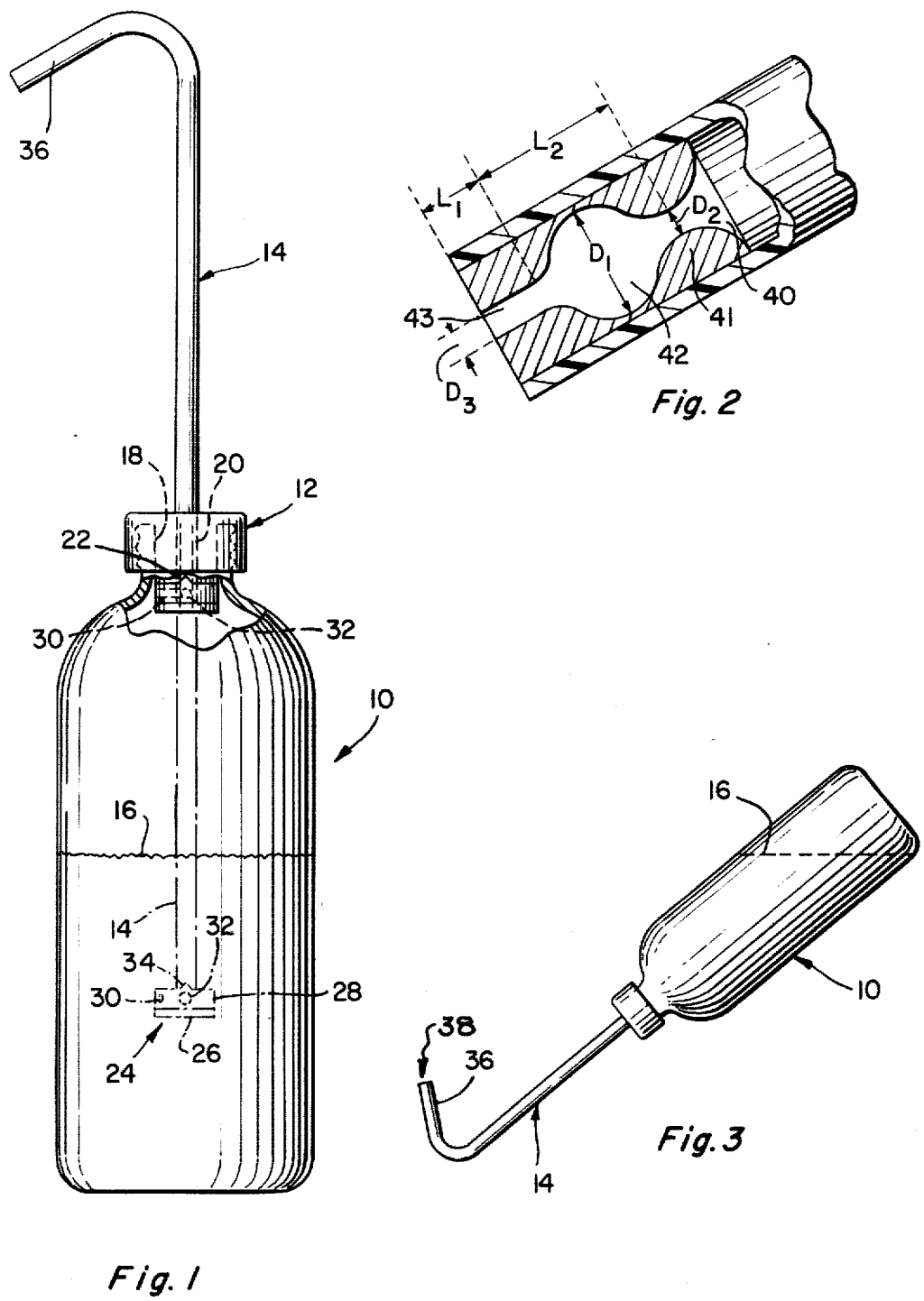
FIG. 1 is a partly cross-sectional view of a container-dispenser for carrying a composition in accordance with the present invention.
FIG. 2 is an enlarged cross-sectional view of a detail of the container-dispenser of FIG. 1.
FIG. 3 is a side view of the container-dispenser of FIG. 1, as it appears in proper orientation for use.

Generally, the formulation of the present invention is designed to loosen and to dissolve fecal residue, to adhere to skin surfaces without tackiness and to resist rubbing off by friction with adjacent skin and clothing surfaces, to disinfect and to accelerate healing, to penetrate skin tissues and fissures and to remain therein, to resist dissolution by sweat, to buffer or neutralize sweat and other skin secretions, and to buffer or neutralize fecal residues.

For best results, this formulation comprises the following:

| Ingredients | Percentage By Total Weight |
|---|---|
| Polymeric film former | 0.1 to 2 |
| Lubricant | 0.1 to 2 |
| Surfactant | 0.1 to 1 |
| Disinfectant | 0.01 to 1 |
| Ionizable zinc compound as a healing accelerator | 0.1 to 5 |
| Organic acid | as required to adjust pH to from 4 to 6 |

| Ingredients | Percentage By Total Weight |
|---|---|
| -continued | |
| Water | remainder |

The polymeric film former, lubricant, surfactant, disinfectant, and zinc compound all are water soluble and together operate in accordance with the present invention only if they are present in a combined concentration of less than ten percent by total weight of the formulation. Preferably, this formulation has a viscosity within the range of from 20 to 500 centipoises and, for best results, this formulation has a viscosity within the range of from 100 to 150 centipoises. The essential ingredients of the formulation are the surfactant, the disinfectant, the ionizable zinc compound, and either the polymeric film former or the lubricant, all in the aforementioned proportions.

More specifically, the polymeric film former is a water soluble polyvinyl, for example, polyvinyl alcohol, which, when cast from dilute solution, forms an extremely thin, possibly monomolecular, residual polymeric stratum. The lubricant, for example, is glycerine or a glycerine compound such as glycerine polysorbate, which moistens and softens the coated skin, thereby protecting it from abrasion during application of the formulation and following formation of the residual stratum. The surfactant, for example, is a detergent such as polysorbate, polyethylene glycol, or polypropylene glycol, which emulsifies any of the other ingredients that remain undissolved, thereby preventing their precipitation before use, and facilitates removal of fecal matter during use. The disinfectant, for example, is benzalkonium chloride, which is a cationic surface active agent with potent germicidal properties and sufficiently low toxicity to avoid irritating dry, fissured, or otherwise damaged skin. The ionized zinc, which is the dissolution product of a readily ionizable zinc compound such as zinc chloride or zinc gluconate, is characterized by small molecular dimensions that, in the environment provided by the other agents, enable ready penetration of the fissured skin for unusually efficacious performance of its known healing function. Ordinarily this zinc compound is substantially completely ionized. The organic acid, for example acetic acid, provides the slightly acidic pH necessary to neutralize fecal residues, which normally are characterized by a pH of approximately 6.6 to 7.7 and by substantial amounts of electrolytes, typically sodium, potassium, chlorides, calcium, phosphorous, and nitrogenous compounds.

In a modification of the above formulation, a parasympathomimetic agent, for example a pilocarpine such as pilocarpine chloride or pilocarpine nitrate, is added in a concentration in the range of from 0.01 to 1 percent by total weight of the formulation. This agent causes discharge by the sweat glands and is useful during the post-operative period of a hemorrohoidectomy to lessen sweat inhibition, by which healing is slowed. Thus this modification flushes the contents of the sweat glands in the anorectal region and washes it away, thereby preventing it from entering open fissures or wounds.

In another modification of the above formulation, a chelating agent, for example ethylenediaminetetraacetate (EDTA) is added in a concentration in the range of from 0.01 to 5 percent by total weight of the formulation. This agent attaches itself tenaciously to the ionic zinc to provide chelated zinc, which is a stable compound that prevents the zinc from reacting with other organic molecules and makes the zinc available biologically for healing purposes.

In what is believed to be a less preferred modification of the above formulation, the healing agent is allantoin rather than zinc. This agent stimulates the growth of healthy tissues in the case of suppurating (causing discharge of pus) wounds.

In other modifications of the present invention, various proportions of the aforementioned parasympathomimetic, chelating and allantoin agents are used in combination with each other or with other optional topical anesthetics such as benzocaine or xylocaine.

An exemplary dispenser, for use with the above described formulation in accordance with the present invention, is shown if FIG. 1 as comprising a container 10, a cap 12, and a rigid elongated nozzle 14. Container 10, which carries the above described formulation as at 16, is composed of a pliable polymeric material, for example, polyethylene. The upper mouth of container 10 is externally threaded. Cap 12 is internally threaded so that it can be turned tightly onto the mouth of container 10. Cap 12 has a centrally depending portion 18 having a vertical bore 20 axially therethrough. The medial portion of nozzle 14 is received snugly by bore 20 for reciprocable adjustment between an upper position as shown in full lines and a lower position as shown in phantom lines. Across the bottom face of portion 18 is a radial notch 22 for a purpose now to be explained.

At the lower extremity of nozzle 14 is a valve 24 that includes a lower flange 26, which is fixed to the lower extremity of the nozzle, and an upper annulus 28, which is rotatable about the nozzle and supported on the flange. Annulus 28 has a port 30, which can be rotated between an open position at which it communicates with a port 32 in a wall of nozzle 14 and a closed position at which it is blocked by the wall of nozzle 14. Extending radially along the top of annulus 28 on opposite sides of its central bore are the parts of a ridge 34. When ridge 34 engages notch 22, nozzle 14 can be rotated manually with respect to annulus 28 in order to open or close valve 24. The outer end of nozzle 14 is a reversely bent head 36, which, as shown in FIG. 2, has a particularly designed mouth 38.

Mouth 38 has an inner chamber 40, an inner neck 41, an outer chamber 42, and an outer neck 43. Inner neck 41 separates the inner chamber from the outer chamber. Outer neck 43 is an exit port. As shown, inner neck 41 has a diameter of $D_2$, outer chamber 42 has a diameter of $D_1$ and a length of $L_2$, and outer neck 43 has a diameter of $D_3$ and a length of $L_1$. Preferably, the foregoing dimensions have the following parameters.

$L_1 = D_1$
$L_2 = $ from $2D_1$ to $3D_1$
$D_2 = $ from $0.3$ to $0.5D_1$
$D_3 = $ from $0.05$ to $0.2D_1$ When the dispenser is in the normal operating condition, it is held manually at approximately a 45 degree angle as shown in FIG. 3 with mouth 38 directed toward the anorectal region. The foregoing dimensions establish a venturi configuration. When the bottle is squeezed, the solution (an incompressible fluid) is forced into the venturi chamber by the air pressure (a compressible fluid) inside the polyethylene bottle. The dynamic characteristics of the squeeze bottle are such that energy can be stored in the polyethylene structure itself. This serves two purposes. (1) The stream emerging from the nozzle is steady and even. The pressure fluctuations are dampened by the energy stored in the bottle itself. (2) The stream can be aimed at the target and held in that position without difficulty. (If we were to use a syringe, i.e. a rigid container, and were to force out a stream under steady pressure, it would be difficult to duplicate this feat without a steady mechanical drive.) This structure is analogous to a rubber balloon where inflation stores energy in the rubber structure itself. If this pressure is released through a small-bore nozzle, a steady state can be achieved for the duration of the positive pressure inside the balloon.

To obtain maximal function, i.e. the most advantageous operation with the minimal amount of energy, the variables must be matched: bottle volume, wall thickness, venturi bore, venturi chamber, etc. For example, a small bottle, say 15 or 30 ml would not function optimally unless the bore of the venturi (dimension $D_3$) (FIG. 1) is reduced to about 0.5 mm diameter. This small bottle then would be capable of producing a free stream of 5 meters in length. This demonstrates that the choice of the dimensional variables is interdependent and that with every change in bottle volume or material (polyethylene, polypropylene), the variables must be matched or tuned to provide the most beneficial pressure to stream ratio. This "tuning" can be done empirically but it can also be predicted mathematically by plotting stream length vs. bottle characteristics (modulus of elasticity of the material, wall thickness, bottle volume, venturi $D_1$, $D_2$, $D_3$, etc.) of 3 or more given bottles of the same material. On this basis, the dimensional characteristics are influenced by the following factors. $L_1$ is critical because this is the minimum length to establish a collected beam (too long an $L_1$ results in friction loss). $L_2$ is not critical. $D_1/D_2$ is critical. $D_1/D_3$ is critical. All must be tuned to the material and dimensions of the bottle itself.

Under these circumstances, when container 10 is squeezed manually with an ordinary manual pressure of from 10 to 20 pounds, a powerful jet stream is emitted, which has a transverse spread of less than ¼ inch per longitudinal foot of the jet stream. This powerful jet of the aforementioned formulation is capable of removing fecal and sweat residues from the anorectal region and leaving a thin pharmaceutical film in their place.

The following non-limiting examples further illustrate the formulation of the present invention.

EXAMPLE 1

The following formulation was prepared:

| | |
|---|---|
| Polyvinyl alcohol (3% aqueous solution) | 50 ml |
| Glycerine | 25 ml |
| Concentrated acetic acid | 1 ml |
| Benzalkonium chloride concentrate (17%) | 0.1 ml |
| Zinc chloride (10% aqueous solution) | 25 ml |
| Polysorbate | 50 ml |
| Polypropylene glycol | 50 ml |
| Water to make total of 1000 ml | Remainder |

There were no alcohols, antibiotics, hexachlorophene, and no prescription drugs. When applied as a jet from the above described dispenser, fecal and sweat residues were removed and replaced by a thin aqueous film of slightly acidic pH, which dried rapidly, particularly when patted with toilet tissue. The film had a significant immediate soothing and healing effect on damaged skin in the anorectal region and, particularly, on hemorrhoidal tissue. It stopped rectal itching instantaneously without use of topical anesthetics.

EXAMPLE 2

A formulation corresponding to that of Example 1 was prepared except that 0.05 ml of water was replaced by ethylenediaminetetraacetate in like amount. Beneficial results were achieved.

EXAMPLE 3

A formulation corresponding to that of Example 1 was prepared except that the zinc chloride solution was replaced by a like amount of allantoin. Beneficial results were achieved.

OPERATION

In practice, immediately following defecation or at any other time, the user withdraws nozzle 14 from container 10 in order to engage notch 22 and ridge 34 and rotates nozzle 14 with respect to container 10 until ports 30 and 32 are aligned. Under these conditions, an open path exists for formulation 16 through nozzle 14 and mouth 38. With nozzle 14 generally pointed downwardly and rearwardly between his or her thighs, mouth 38 is directed toward and in proximal relation with the anorectal region. The user now squeezes container 10 in order to generate a powerful jet that loosens and dissolves fecal residue, disinfects and neutralizes the anorectal region, and leaves a thin film residue, which dries spontaneously with minimum patting or without patting by toilet tissue. The process is continued as needed with daily regularity for prophylactic or therapeutic purposes.

Since certain changes may be made in the above described compositions, products and processes without departing from the scope of the present invention, it is intended that all matter herein disclosed be interpreted in an illustrative and not in a limiting sense.

What is claimed is:

1. A product comprising a dispenser for containing and dispensing a formulation therewithin for application to the anorectal region:
   (a) said dispenser including container means and nozzle means, said dispenser being composed of a flexible polymer, said container means being operatively associated with pressure means for ejecting said formulation from said container means through said nozzle means, said nozzle means having a reversely directed mouth so as to be directed toward the anorectal region when said dispenser is held manually;
   (b) said formulation being an aqueous dispersion of agents including a film former, a surfactant, and a healing accelerator, said agents being present in concentrations that total less than ten percent;
   (c) the viscosity of said formulation being within the range of from 20 to 500 centipoises, said mouth of said nozzle being characterized by a stream inducing orifice, said viscosity and said orifice being related to produce a jet when pressure is applied to said formulation within said dispenser;
   (d) said mouth being characterized by a venturi configuration having an inner chamber, an inner neck of diameter $D_2$, an outer chamber of diameter D and length $L_2$, and an outer neck of diameter $D_3$ and length $L_1$, such that $L_1 = D_1$, $L_2 =$ from 2D to $3D_1$, $D_2 =$ from 0.3 to $0.5D_1$, and $D_3 =$ from 0.005 to $0.2D_1$.

2. The product of claim 1 wherein said mouth is characterized by a venturi configuration having an inner chamber, an inner neck of diameter $D_2$, an outer chamber of diameter D and length $L_2$, and an outer neck of diameter $D_3$ and length $L_1$, such that $L_1 = D_1$, $L_2 =$ from 2D to $3D_1$, $D_2 =$ from 0.3 to $0.5D_1$, and $D_3 =$ from 0.005 to $0.2D_1$.

3. A process for anorectal care comprising as steps:
   (a) directing to the skin of the anorectal region a jet of a composition including, as agents in an aqueous vehicle, a film former, a surfactant, and a healing accelerator, the pH of said composition being within the range of from 4 to 6 and the viscosity of said composition being within the range of from 20 to 500 centipoises;
   (b) washing fecal and sweat residues from said anorectal region by impact of said jet and dissolution in said aqueous vehicle;
   (c) neutralizing said anorectal region by subjection to said pH of said composition;
   (d) permeating said skin with said healing accelerator; and
   (e) drying the composition in said anorectal region in order to leave a thin film of residue, said film being water permeable.

4. The process of claim 3 wherein said film former includes a water soluble polymer.

5. The process of claim 3 wherein said surfactant includes a detergent.

6. The process of claim 3 wherein said healing accelerator includes an ionizable zinc compound.

7. The process of claim 3 wherein zinc ions are in aqueous solution.

8. The process of claim 3 wherein said healing accelerator includes allantoin.

9. The process of claim 3 wherein the pH of said solution is in the range of from 4 to 6.

10. The process of claim 3 wherein said agents include a lubricant.

11. The process of claim 3 wherein said agents include a disinfectant.

12. The process of claim 3 wherein said agents include a parasympathomimetic.

13. The process of claim 3 wherein said agents include a chelating agent.

* * * * *